United States Patent
Kostka et al.

(10) Patent No.: US 7,399,730 B2
(45) Date of Patent: Jul. 15, 2008

(54) ENHANCING PLANT PRODUCTIVITY BY IMPROVING THE PLANT GROWTH MEDIUM ENVIRONMENT WITH ALKYL ETHERS OF METHYL OXIRANE-OXIRANE COPOLYMER SURFACTANTS

(75) Inventors: Stanley J. Kostka, Cherry Hill, NJ (US); Gregor Schuermann, Schwetzingen (DE)

(73) Assignee: Aquatrols Corporation of America, Inc., Paulsboro, NJ (US)

(*) Notice: Subject to any disclaimer, the term of this patent is extended or adjusted under 35 U.S.C. 154(b) by 486 days.

(21) Appl. No.: 11/095,409

(22) Filed: Mar. 31, 2005

(65) Prior Publication Data

US 2005/0221992 A1 Oct. 6, 2005

Related U.S. Application Data

(60) Provisional application No. 60/559,051, filed on Apr. 2, 2004.

(51) Int. Cl.
*A01N 25/02* (2006.01)
*A01N 25/08* (2006.01)

(52) U.S. Cl. .................................... 504/362
(58) Field of Classification Search ................ 504/362
See application file for complete search history.

(56) References Cited

U.S. PATENT DOCUMENTS

| | | | |
|---|---|---|---|
| 4,187,384 A | 2/1980 | Platz et al. | |
| 4,587,365 A | 5/1986 | Anchor | |
| 4,624,803 A | 11/1986 | Balzer et al. | |
| 4,922,029 A * | 5/1990 | Birnbach et al. | 568/616 |
| 5,629,260 A | 5/1997 | Utz et al. | |
| 6,117,820 A | 9/2000 | Cutler et al. | |
| 6,165,939 A | 12/2000 | Agbaje et al. | |
| 6,184,182 B1 | 2/2001 | Gillespie et al. | |
| 6,241,994 B1 | 6/2001 | Lee et al. | |
| 6,245,713 B1 | 6/2001 | Brinker et al. | |
| 6,407,042 B1 | 6/2002 | Ward et al. | |
| 6,475,953 B1 | 11/2002 | Ward et al. | |
| 6,479,434 B1 | 11/2002 | Gillespie et al. | |
| 6,479,437 B1 | 11/2002 | Bratz et al. | |
| 6,500,783 B1 | 12/2002 | Bryson et al. | |
| 2003/0073583 A1* | 4/2003 | Kostka et al. | 504/362 |

OTHER PUBLICATIONS

Federal Register: Mar. 5, 1999 (vol. 64, No. 43)] [Rules and Regulations] [p. 10567-10571] From the Federal Register Online via GPO Access [wais.access.gpo.gov][DOCID:fr05mr99-7].*

* cited by examiner

*Primary Examiner*—Johann Richter
*Assistant Examiner*—Courtney A Brown
(74) *Attorney, Agent, or Firm*—John A. Shedden

(57) ABSTRACT

Improved plant growth is realized especially with turf grasses by using an enhanced plant growth medium prepared by adding a bioefficacious amount of $C_1$-$C_4$ alkyl ether of methyl oxirane-oxirane copolymer that, serendipitously reduces the water repellency of the medium.

19 Claims, 8 Drawing Sheets

US 7,399,730 B2

ENHANCING PLANT PRODUCTIVITY BY IMPROVING THE PLANT GROWTH MEDIUM ENVIRONMENT WITH ALKYL ETHERS OF METHYL OXIRANE-OXIRANE COPOLYMER SURFACTANTS

The present application claims the benefits accorded under 35 U.S.C. 119(e) of prior provisional application No. 60/559,051 filed 2 Apr. 2004.

FIELD OF THE INVENTION

The present invention generally relates to a method for enhancing the productivity of plants. More particularly, this invention relates to providing an improved plant growth medium in and around the plant rootzone by the application to the medium of certain ethers of methyl oxirane-oxirane copolymer surfactants. This process is especially efficacious in quickly enhancing the infiltration of water into and the uniformity of the water throughout the medium as well as improving the long-term hydrophilicity of water repellent medium.

BACKGROUND OF THE INVENTION

The majority of plants obtain most of their nutritional requirements from the plant medium in which they are growing. The plant growth medium, is characterized by its capacity to exchange ions. Plant roots derive their nutrients from the growth medium by the exchange of nutrient ions within the medium to sites on the roots of the plants. In the absence of an aqueous transfer medium, i.e., moisture, plants have not been able to grow well or even survive.

Agriculturalists and agronomists have to work with all types of plant growth media such as sand, natural earth, horticultural soils, and various soil-mimicking, soil-less plant culture substrates, all of which will be generically referred to hereinafter as soil; however, the bane of essentially all who work in the field is water repellent soil (WRS). Water repellent soil retards water infiltration into the soil matrix; often exists as local dry spots (LDS); and can render entire areas of the upper layers of the soil substrate essentially impervious to water penetration. Under rainfall or irrigation conditions, dire environmental consequences can result from the water repellency of the soil, such as surface runoff or leaching into pristine areas and/or potable reservoirs, of water and aqueous compositions containing pesticides and/or fertilizers.

A characteristic of soils, especially field soils, is that during a dry period, i.e., a period of days or weeks with very little to no rain, the moisture content of the soil can reach a very low level at which point the soil becomes unable to be re-wetted by the application of water via rain or irrigation alone and thus the soil becomes no longer an acceptable plant growth medium. It is understood by those in the art that the soil has dropped below the Critical Water Content (CWC).

Water repellency of a soil is not only a function of the initial water content of the soil, but is also a function of soil particle size, e.g., sands are more prone to water repellency than clays, as well as the type of organic matter incorporated in the soil. This organic matter induces water repellency in the soils in various ways, such as by providing hydrophobic organic substances leached from plant litter; organic substances that have been irreversibly dried; and/or hydrophobic microbial by-products.

Before water will evenly infiltrate into or percolate through a soil matrix, there must be a continuous film of water on the soil particles. In other words, the soil must first be wetted before water will flow through it. Agriculturalists have realized that the Critical Water Content level can be modified and the water repellency of these soils can be reduced through the use of wetting agent surfactant compositions; especially compositions containing nonionic surfactants. However, the degree of efficacy among surfactant chemistries and formulations has varied significantly. To ameliorate water repellency and/or to enhance infiltration, high rates of wetting agents are frequently applied; such elevated rates may become injurious to plants. For example, the surfactants being utilized to increase the moisture levels in soil tend to not penetrate deeply into the soil, i.e., they remain in the upper regions of the soil and biodegrade rapidly thus requiring numerous applications. Furthermore, the increase in concentration of the surfactants currently deemed necessary in initially water repellent soil often have a severe, negative impact on the surrounding environment, especially toxicity to plant tissues, and have a negative effect on the plant growth properties of the soil.

"Although an increasing number of researchers are aware of the occurrence and consequences of water repellency in a wide range of soils, it is still a neglected field in soil science." (Dekker et al., International Turfgrass Society Research Journal, Volume 9, 2001, pages 498-505)

Agriculturalists continue to seek a composition which, when applied to a plant growth medium susceptible to unacceptable drying, would i) rapidly and uniformly penetrate deeply into the medium matrix; ii) enable significant re-wetting of the medium, i.e., modify the Critical Water Content especially around the plant rootzone; iii) provide a long lasting effect to reduce the necessity for frequent applications; and iv) be effective at lower concentration levels than surfactants currently being used, thus reducing the negative impacts that any chemicals can have on the environment.

The instant invention provides the above-enumerated advantages and, serendipitously, enhances plant growth, especially plant density, color, and quality without the need for fertilizer applications.

BRIEF DESCRIPTION OF THE INVENTION

SUMMARY OF THE INVENTION

Figure 1:
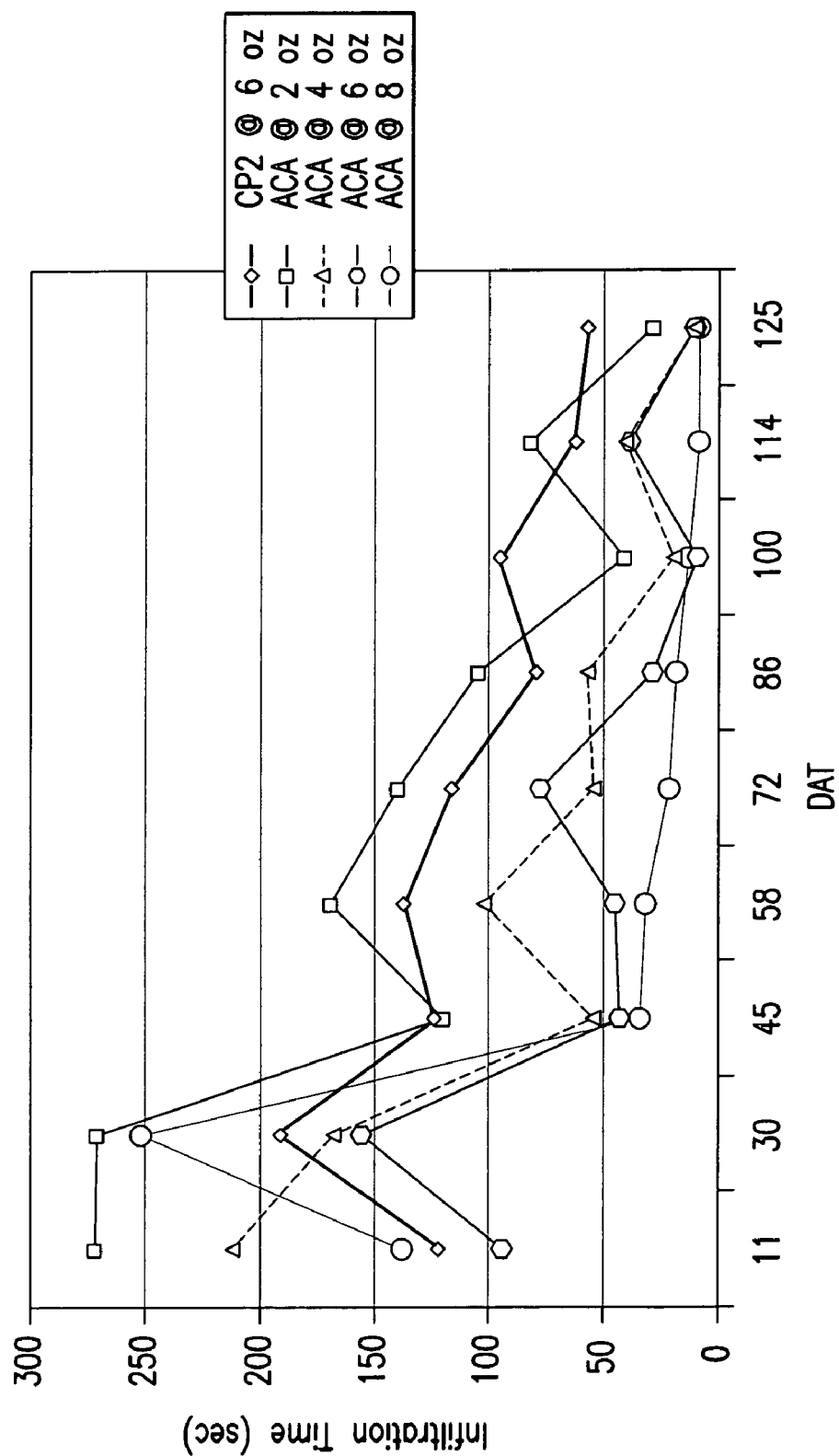
FIG. 1 is a graphical depiction of the WDPT infiltration time results obtained by the tests in Example V and set forth in Table V.

The instant invention provides a process for enhancing plant productivity by improving certain desirable characteristics of the plant growth medium. The process consists of applying to the medium an effective amount of a composition comprising a $C_1$-$C_4$ alkyl ether of methyl oxirane-oxirane copolymer. These compositions unexpectedly exhibit significantly enhanced aqueous re-wetting infiltration rates, depths, and longevity, especially in water repellent soil, over that previously achieved in the art.

DETAILED DESCRIPTION OF THE INVENTION

The instant invention specifically relates to the discovery that plant growth medium can be significantly improved by the addition to the medium of a bioefficaciously effective amount of $C_1$-$C_4$ alkyl ether of methyl oxirane-oxirane copolymer. It has been found that these surfactants enable moisture to penetrate rapidly and deeply into the medium matrix; and can realize significant re-wetting of an initially dry medium, especially medium identified as highly water repellent. The compositions also exhibit a slower biodegradability than that of the hydroxyl terminated methyl oxirane-oxirane copolymers and thus provide inherent slow release properties. Finally, and serendipitously, the resulting growth medium produces plants, especially monocots, and most especially grasses with vastly improved quality and density as compared to that achieved with the similar, prior art utilized hydroxyl terminated methyl oxirane-oxirane copolymer agricultural wetting agents.

Additionally, it has been found that compositions containing these compounds are highly efficacious over a wide range of concentrations which is of critical importance in achieving maximum agronomic and/or hydrological benefit while minimizing negative environmental impact.

$C_1$-$C_4$ alkyl ethers of methyl oxirane-oxirane copolymers can be readily accomplished by etherification procedures known in the art, as for example taught in U.S. Pat. No. 4,922,029. As a specific example, conversion of a methyl oxirane-oxirane copolymer having hydroxyl termination to a methyl ether of the copolymer is readily effected by reacting it with sodium hydroxide and methyl chloride, although it is possible to use metallic sodium in place of the sodium hydroxide, and/or other methyl halides or dimethyl sulfate in place of methyl chloride. In any event, the methyl ether formation is accompanied by the formation of a by-product salt that is separated from the product. The salt can be separated by conventional means such as filtration, decantation, extraction, and/or distillation. In some cases, it is advantageous to conduct the methylation in two or more steps with salt separation after each step.

It has been suggested by the prior art that ethers of methyl oxirane-oxirane copolymers can be used as solvents, industrial cleaners, hydraulic fluids, accelerators or catalysts for ionic organic reactions, lubricants for synthetic textiles, solubilizing agents for inorganic salts, and adjuvants to enhance pesticidal, i.e., injurious activity in foliar applications—the antithesis of the current invention; however, the re-wetting improvements realized by applying the compounds of this invention to plant growth medium, and/or water repellent soils and the resulting enhancement in the quality and density of the plants utilizing such an improved medium matrix are wholly unexpected since there is nothing in the prior art to suggest that $C_1$-$C_4$ alkyl ethers of methyl oxirane-oxirane copolymers could be used in such a manner or would achieve such surprising results.

The $C_1$-$C_4$ alkyl ethers of methyl oxirane-oxirane copolymers of the instant invention include, before etherification, the straight polymeric glycols obtained, for example, by the addition of ethylene oxide on propylene oxide structurally depicted as $HO(CH_2CH_2O)_x(CH(CH_3)CH_2O)_y(CH_2CH_2O)_z H$. The identical or different integers x,y, and z individually are greater than or equal to zero such that the desired propylene oxide and ethylene oxide mass average molecular weights and percentages are obtained. The polymethyloxirane cores, being hydrophobic, have units at least about 9, and are usually in the range of from about 950 to about 4,000 mass average molecular weight. The oxirane is added to the core at from about 10 weight percent to about 80 weight percent. In a preferred embodiment, the polymethyloxirane core mass average molecular weight is from about 1500 to about 2000 with oxirane addition of from about 20 to about 40 weight percent.

It has been observed in the art that soil wetting speed tends to increase (wetting time decreases) with increasing hydrophobe molecular weight and decreasing HLB value within each particular hydroxyl terminated methyl oxirane-oxirane copolymer structural type, i.e., the straight copolymers; the reverse copolymers; the diamine-based copolymers; and the diamine-based reverse copolymers.

Stated another way, generally hydroxyl terminated methyl oxirane-oxirane surfactants with a lower HLB value and a higher average molecular weight show the shortest infiltration times through a column of hydrophobic soil. This trend holds true for all four surfactant structural types and is expected to hold true for the alkyl ethers of the methyl oxirane-oxirane copolymers of this invention.

The preferred alkyl ethers of methyl oxirane-oxirane copolymers for use in this invention are those having an HLB value less than or equal to 10; an average molecular weight of from 2,000 to 8,000 and a percent hydrophile of from less than 10 to 40. The most preferred block copolymers are those having an HLB value less than or equal to 10; an average molecular weight of from 2,000 to 8,000 and a percent hydrophile of from less than 10 to 20.

The concentration of the polymer ether wetting agent compositions of this invention in the aqueous formulations to be applied to the plant growth medium is not critical. Wetting agent composition levels of up to 200,000 ppm are contemplated in this invention for those concentrations are non-injurious to most plants. Thus, the concentration of the polymer wetting agent in the aqueous formulations will range from about 200,000 to about 2 ppm; preferably from about 120,000 to about 5 ppm.

The most efficacious application rates of the polymer ethers on plant growth media have been found to be in the range of from about 0.001 to about 128 fluid ounces per 1000 square feet; preferably from about 0.1 to about 32 fluid ounces per 1000 square feet; and most preferably from about 0.2 to about 16 fluid ounces per 1000 square feet. These application rates reflect individual applications or the cumulative amounts resulting from multiple applications within a limited but bioefficacious period of time.

One of the surprising features of the use of these alkyl ethers of the methyl oxirane-oxirane copolymer compositions is the outstanding effectiveness at very low concentrations: a highly desirable environmental property. In any event, appropriate concentration levels are easily determined by those skilled in the art.

As an aside, hydroxyl terminated methyl oxirane-oxirane copolymers tend to biodegrade fairly quickly in the field for microbes have developed a biosynthetic ability to utilize them. The microorganisms attack the hydroxyl groups from each end. They do not appear to cleave the molecular chain between the repeating blocks. When the backbone of these methyl oxirane-oxirane copolymers are terminated as alkyl ethers, it has been found that there occurs a less rapid biodegradability resulting in a slow release phenomenon. In fact, the biodegradability of the methyl ethers of the methyl oxirane-oxirane copolymers have been found to be fairly moderate, i.e., about 30 to 40% $CO_2$ after 28 days.

Results realized by using the instant invention are exemplified below; however definitions and the test procedures utilized will first be clarified.

The commonly accepted method of classifying the water repellency of soils is through the use of the Water Droplet Penetration Test (WDPT). In this test, drops of distilled water are placed on the smoothed surface of a soil sample, and the time that elapses before the drops are completely absorbed is determined. All WDPTs are conducted under controlled conditions usually at a constant temperature of about 20° C. and a relative air humidity of about 50%. These tests are normally replicated at least three times.

To conduct the WPDT on field samples, soil cores are collected with a 2 cm soil probe to a depth of 15 cm. Five cores are collected from each plot. Cores are dried for 2 weeks at room temperature. The cores are placed horizontally on a workbench and a 35 microliter droplet of distilled water is dispensed via a pipette and placed at 1 cm intervals along the core starting at the thatch-air interface and ending at 6 cm. A stopwatch is used to determine the length of time (in seconds) it takes for the water droplet to completely penetrate the soil core. Although soil water repellency is a relative property, varying in intensity, it is generally recognized in the art that a soil is to be considered water repellent if the WPDT exceeds five seconds. This allows soils to be qualitatively classified and referred to as being either wettable or water repellent. The instant invention is especially effective in rapidly increasing the hydrophilicity of water repellent soil.

Another method used to determine the degree of water repellency of a plant growth medium is the Molarity of Ethanol Droplet test (MED). This test determines the molarity at which an aqueous ethanol droplet will infiltrate a soil in 10 seconds. As this is one of the simplest and least time consuming methods of determining water repellency, it is commonly used. It relies on the fact that with increasing concentration, the ethanol lowers the liquid-substrate contact angle thereby increasing the rate of infiltration into the soil. Thus, any hydrophobic coatings on the growth medium particles are rapidly wetted by the ethanol and the ability of the medium to wet increases as the concentration of ethanol in the aqueous solution increases. Water repellency can begin to be a concern as the molarity exceeds about 2.1 and is considered quite severe when greater than 3.0.

A simple laboratory "Straw Test" developed by Aquatrols Corporation of America can be used to record the initial effectiveness of a wetting agent composition on water repellent soil. (International Turfgrass Society Research Journal 7. Intertec Pubishing Corp. 1993 Chapter 67, pages 485-488). The Straw Test consists of taking clear plastic drinking straws (19 cm. in length and 0.5 cm. in diameter) and folding them in the center to give a sharp "V" shape, i.e., no flat crimps. Adhesive tape is used to hold the two arms of the straw in this "V" position. One arm of the straw is filled with hydrophobic soil while tapping the straw gently on a solid surface to ensure even settling of the soil in the straw. The resulting soil column is plugged with cotton and the straws arranged on a flat support. Test solutions at selected concentrations are introduced individually into each of the empty arms of the straws with a pasteur capillary pipet. The arm containing the hydrophobic soil column is laid horizontally on the support surface; the adhesive tape removed; and the arm lowered toward the support surface until the arm is at a 25° angle to the surface.

A wedge or support is fixed to the surface to ensure that the straw angle is maintained throughout the test. A stopwatch is started as soon as a test solution comes in contact with the hydrophobic soil and the time to wet a 6 cm. length of the soil column is recorded. Distilled water is usually used as a standard. This straw test is sensitive to concentrations as low as 10 ppm.

One method of evaluating field plots, especially turfgrass field plots, is for agronomists and/or agricultural researchers to assign a numerical "quality" rating to the plants in each treatment area. A quality rating is largely based on the agronomist's/researcher's experience but takes into account a myriad of factors. Factors considered include turf color, density, turgidity, lack of disease or localized dry spot, and how upright the leaf blades stand. Ratings are generally based on a scale of 1 to 9 and this is the scale used in the following examples, where 1 would be dead/brown turf, 6.5 would be a minimally acceptable rating for golf or other fine turf situations, and 9 would be the highest quality turf possible.

By the term "re-wettingly effective amount" is meant that the amount of the alkyl ether of the methyl oxirane-oxirane copolymer in contact with the soil is such that there is a measurable enhancement of the wetting characteristics of the soil.

By the term "bioefficaciously effective amount" is meant that the amount of the alkyl ether of the methyl oxirane-oxirane copolymer in contact with the soil is such that there is a measurable enhancement of plant growth, e.g., quality and/or density resulting from the use of the treated soil.

Other than in the operating examples, or where otherwise indicated, all numbers expressing quantities of ingredients or reaction conditions used herein are to be understood as modified in all instances by the term "about". All measurements in ounces are meant to reflect fluid ounces unless otherwise indicated.

The invention will now be described with reference to a number of specific examples which are to be regarded solely as illustrative of the methods and compositions of this invention and not as restrictive of the scope thereof. All percentages are by weight unless otherwise indicated.

EXAMPLE 1

A micro-scale Soxhlet extraction was conducted using a commercially available, hydroxy terminated methyl oxirane-oxirane copolymer (hereinafter identified as the Comparative Product 1 aka CP1) and a methyl ether of a methyl oxirane-oxirane copolymer (identified herein as ACA), both having a molecular weight of about 2,500, on water repellent soil samples to determine the relative ability of the compounds to solubilize components of a soil sample.

Hydrophobic soil was obtained from a site in the New Jersey Pine Barrens and dried down in a convection oven for seven days at 70° C. The soil was then sieved to remove unwanted debris and achieve a particle size of less than 500 micrometers. Approximately 2.50% surfactant by weight was loaded onto the soil and allowed to air-dry.

A micro-scale Soxhlet extraction apparatus was constructed comprising three primary components, to wit, a central chamber for holding a cellulose extraction sample thimble and having a sidearm for siphoning solvent and extract back down to a round-bottom distillation flask on which the central chamber is mounted. The distillation flask has a side arm that carries the vapors up to a condenser that is mounted directly above and attached to the central chamber.

Four grams of the surfactant-treated soil was placed in the 10×50 mm thimble and extracted with distilled water as solvent using the above apparatus. The thimble is first placed in the central chamber and the water is heated in the distillation flask. The vapors rise through the side arm of the flask and enter the condenser where they liquify, dropping from the tip of the condenser into the thimble containing the surfactant treated soil. The liquid remains in the central chamber, increasing in volume and extracting material off of the treated soil until the liquid reaches the top of the sidearm. At this point, hydrostatic pressure inside the chamber causes the water and extract to be siphoned back to the distillation flask. This process is continued until all of the extract has been removed from the treated soil. The standard operating procedure for this process is to allow one hour of extraction time. Percent solids analysis was used to quantify the amount of non-volatile material that was removed from the surfactant treated soil. This data was then converted to percent yield, which is a ratio of the amount extracted versus the total amount of surfactant that could have been extracted expressed as a percentage. The results are set forth in Table I below.

TABLE I

| Product | Percent Yield |
|---|---|
| CP1 | 84.74 |
| ACA | 200.86 |

The above results show that more solids were extracted from the hydrophobic soil that had been treated with the methyl ether of a methyl oxirane-oxirane copolymer, i.e., ACA than were extracted from the soil that had been treated with the methyl oxirane-oxirane copolymer that was hydoxy terminated. Surprisingly, more solids were extracted from the ACA treated soil than were initially loaded onto the soil. Apparently, the methyl ether terminated copolymer enhanced the solubility of certain compounds within the soil and thus facilitated their removal via extraction.

EXAMPLE II

The water repellent soil which is used in the following tests is made by coating a hydrophilic sand with octadecyl trichloro silane (OTS) as described by Bauters, et al., 1998 Soil Sci. Soc. Am. J. 62: 1185-1190.

Using the aforedescribed Straw Test, the time in seconds for distilled water to infiltrate through a six centimeter column of this water repellent soil is determined through three replications. The results are set forth in Table II.

TABLE II

| Treatment | Replication 1 | Replication 2 | Replication 3 | Average |
|---|---|---|---|---|
| Distilled Water | 604,800 s | 691,200 s | 604,800 s | 633,600 s |

These numbers indicate the base-line hydrophobicity of this mineral soil and serve as the control in the quantification of the performance of wetting agent compositions tested.

Since the infiltration time values obtained with the instant mineral soil prepared above all exceed seven days (86,400 seconds per day), this soil is obviously extremely hydrophobic, i.e., clearly water repellent.

CP1 and ACA in concentrations as indicated below are examined using the aforedescribed Straw Test in order to ascertain the ability of the surfactants to affect the infiltration wetting time of the water repellent soil column described above. The results of the tests are set forth in Table IIA below.

TABLE IIA

| Product | Total Concentration in Water (ppm) | | |
|---|---|---|---|
| | 8000 | 6000 | 4000 |
| ACA | 24.86 | 55.33 | 76.33 |
| CP1 | 44.80 | 62.33 | 97.33 |

EXAMPLE III

A second series of Straw Tests is conducted using extremely water repellent soil prepared by coating a basic sand selected from a different but similar lot to that used in Example II, with octadecyl trichloro silane (OTS) as described in Example II.

CP1 and the ACA in concentrations as indicated below are again examined using the Straw Test in order to ascertain the ability of the surfactants to affect the infiltration wetting rate of a second water repellent soil described above. Each test is replicated three times. The results of the tests in seconds are set forth in Table III below.

TABLE III

| Product | | Total Concentration in Water (ppm) | | |
|---|---|---|---|---|
| | | 8000 | 6000 | 4000 |
| ACA | Replicate 1 | 145 | 150 | 285 |
| | Replicate 2 | 189 | 155 | 122 |
| | Replicate 3 | 175 | 220 | 201 |
| | Average | 170 | 175 | 202 |
| CP1 | Replicate 1 | 227 | 320 | 375 |
| | Replicate 2 | 147 | 220 | 219 |
| | Replicate 3 | 370 | 340 | 315 |
| | Average | 248 | 293 | 303 |

EXAMPLE IV

A third series of Straw Tests is conducted using another highly water repellent soil individually prepared by selecting a third lot of basic sand, similar to the lots used in Examples II and III above, and treating it with OTS as described in Example II above.

CP1 and the ACA in concentrations of 8000 ppm are again examined using the Straw Test in order to ascertain their ability to affect the infiltration wetting rate of the third water repellent soil described above. The test is replicated six times. The results of the tests in seconds are set forth in Table IV below.

TABLE IV

| Product | Rep 1 | Rep 2 | Rep 3 | Rep 4 | Rep 5 | Rep 6 | Average |
|---|---|---|---|---|---|---|---|
| ACA | 10 | 11 | 15 | 14 | 8 | 18 | 12.67 |
| CP1 | 41 | 30 | 28 | 23 | 24 | 42 | 31.33 |

The above Straw Test results clearly show the outstanding and unexpected increases in infiltration rates that can be achieved with the methyl ether of the methyl oxirane-oxirane copolymers of this invention compared to similar hydroxy terminated copolymers at the concentrations tested when they are applied to water repellent soil.

EXAMPLE V

Field trials were conducted on a native sandy soil in order to compare the relative effect on water repellency in the soil realizable with ACA, the methyl ether of methyl oxirane-oxirane copolymer of Example 1 versus that obtainable with a commercial surfactant which is a 95:5 percent blend of a hydroxy-terminated, polymeric polyoxyalkylene and oxoalkenyl hydroxy polyoxyalkane diyl respectively soil surfactant (hereinafter referred to as Comparative Product 2 aka CP2). The CP2 was applied at a rate of 6 oz/1000 sq ft and the ACA was applied at rates of 2, 4, 6, and 8 oz/1000 sq ft. Each treatment was applied monthly over approximately a four month period. The trials were conducted on fairway height bentgrass. Two thousand individual data points were collected every two weeks; about 18,000 data points in total. The infiltration times for the samples were determined by the WDPT procedure. The averaged results from these field trials are set forth in Table V and graphically depicted in FIG. 1 as infiltration times in seconds versus days after initial treatment (DAT).

Examples V and VI illustrate the superiority of the methyl ether of the methyl oxirane-oxirane copolymer over the CP2 and CP3 technologies in the reduction and management of soil water repellency. The alkyl ethers of the methyl oxirane-oxirane copolymers of this invention can be applied at significantly lower rates than that of the CP2 and CP3 surfactants and still achieve performance equal to and even exceeding that of those commercial copolymer surfactants. The trials also show that the effectiveness in reducing the soil water repellency correlated to the treatment rate, i.e., as the methyl ether of the methyl oxirane-oxirane copolymer rate increased, the efficacy in reducing the soil water repellency also increased.

TABLE V

WDPT Infiltration Times (sec)

| Product/DAT | 11 | 30 | 45 | 58 | 72 | 86 | 100 | 114 | 125 |
|---|---|---|---|---|---|---|---|---|---|
| CP2 @ 6 oz | 122 | 191 | 124 | 137 | 116 | 79 | 95 | 62 | 57 |
| ACA @ 2 oz | 272 | 271 | 120 | 169 | 140 | 105 | 41 | 82 | 28 |
| ACA @ 4 oz | 212 | 168 | 54 | 102 | 54 | 57 | 19 | 40 | 10 |
| ACA @ 6 oz | 94 | 156 | 43 | 45 | 77 | 28 | 9 | 38 | 10 |
| ACA @ 8 oz | 138 | 252 | 34 | 31 | 21 | 18 | 13 | 8 | 8 |

EXAMPLE VI

Figure 2:
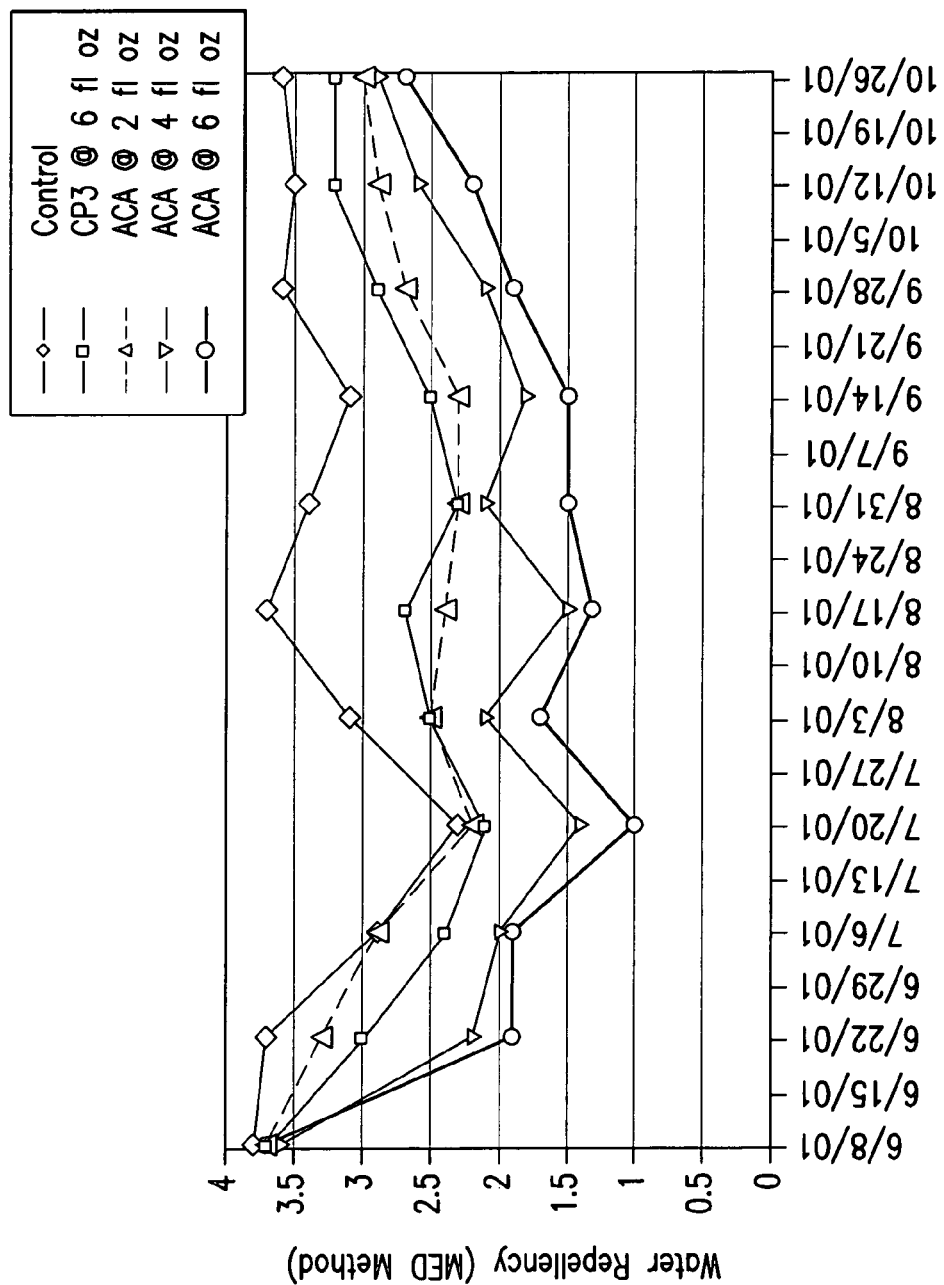
FIG. 2 is a graphical depiction of the MED infiltration time results obtained by the tests in Example VI and set forth in Table VI.

A set of field trials were conducted in order to compare the relative effect on water repellency in the soil realizable with ACA, the methyl ether of the methyl oxirane-oxirane copolymer of Example 1 versus a) control and b) that obtainable with a commercial surfactant which is a product that is 100% hydroxy terminated, polymeric polyoxyalkylenes (Comparative Product 3 hereinafter referred to as CP3) The CP3 was applied at a rate of 6 oz/1000 sq ft and the ACA was applied at rates of 2, 4, and 6 oz/1000 sq ft. This trial was conducted on a USGA specification sand rootzone that was water repellent. The turf type was bentgrass. Over a period of four to four and one-half months, 2000 individual data points were collected every two weeks; about 18,000 data points in total. The infiltration times for the samples was determined by the MED method. The averaged results from these field trials are set forth in Table VI and graphically depicted in FIG. 2 as Water Repellency (Molarity) versus Dates.

EXAMPLE VII

A four month field trial was conducted on a water repellent sand green built to U.S. Golf Association (USGA) specifications. The turf type was bentgrass. The trial was designed to assess the effectiveness of ACA compared to that achieved via the use of a commercial surfactant in providing a season long reduction in the water repellency of this initially water repellent turf medium. The comparative commercial surfactant was a composition believed to be comprised of a 90:10 blend of a hydroxy terminated, straight methyl oxirane-oxirane copolymer having a 10% hydrophile, a molecular weight of approximately 2,000, and an HLB of 3 and an alcohol ethoxylate respectively. This commercial surfactant is hereinafter identified as Comparative Product 4 aka CP4. The ACA was applied at the 4 oz/1000 sq ft rate four times during the season. The CP4 was applied at a rate of 8 oz/1000 sq ft at the beginning of the trial period and one week later. The water repellency results of these tests over the four-month season as

TABLE VI

Water Repellency (Molarity)

Figure 3:
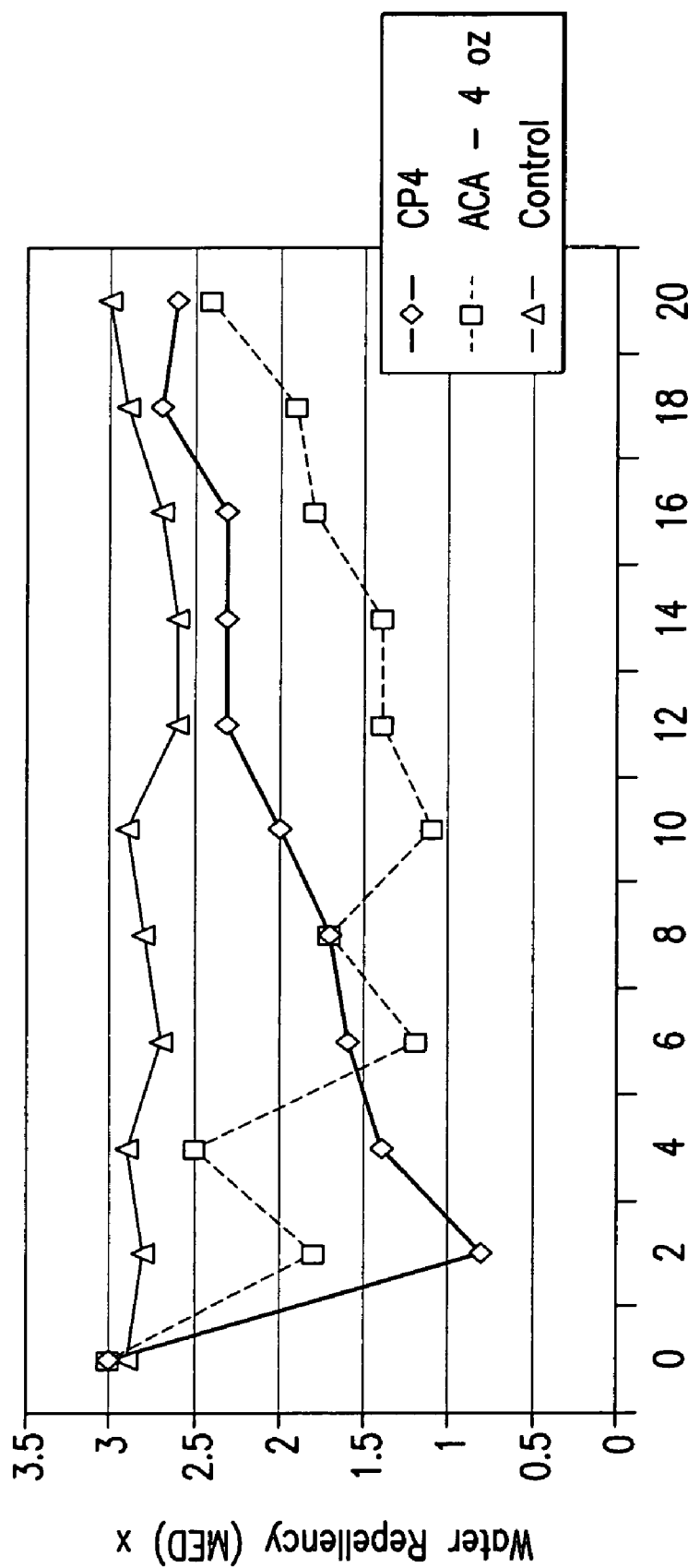
FIG. 3 is a graphical depiction of the MED infiltration results obtained on bentgrass turf explained in Example VII and set forth in Table VII.

| Product/Date | Jun 8 | Jun 22 | Jul 6 | Jul 20 | Aug 3 | Aug 17 | Aug 31 | Sep 14 | Sep 28 | Oct 12 | Oct 26 |
|---|---|---|---|---|---|---|---|---|---|---|---|
| Control | 3.8 | 3.7 | 2.9 | 2.3 | 3.1 | 3.7 | 3.4 | 3.1 | 3.6 | 3.5 | 3.6 |
| CP3 @ 6 oz | 3.7 | 3.0 | 2.4 | 2.1 | 2.5 | 2.7 | 2.3 | 2.5 | 2.9 | 3.2 | 3.2 |
| ACA @ 2 oz | 3.7 | 3.3 | 2.9 | 2.2 | 2.5 | 2.4 | 2.3 | 2.3 | 2.7 | 2.9 | 3.0 |
| ACA @ 4 oz | 3.6 | 2.2 | 2.0 | 1.4 | 2.1 | 1.5 | 2.1 | 1.8 | 2.1 | 2.6 | 2.9 |
| ACA @ 6 oz | 3.7 | 1.9 | 1.9 | 1.0 | 1.7 | 1.3 | 1.5 | 1.5 | 1.9 | 2.2 | 2.7 | determined by the MED method are set forth in Table VII below and graphically depicted in FIG. 3.

TABLE VII

| Product/Weeks | 0 | 2 | 4 | 6 | 8 | 10 | 12 | 14 | 16 | 18 | 20 |
|---|---|---|---|---|---|---|---|---|---|---|---|
| Control | 2.9 | 2.8 | 2.9 | 2.7 | 2.8 | 2.9 | 2.6 | 2.6 | 2.7 | 2.9 | 3.0 |
| CP4 | 3.0 | 0.8 | 1.4 | 1.6 | 1.7 | 2.0 | 2.3 | 2.3 | 2.3 | 2.7 | 2.6 |
| ACA | 3.0 | 1.8 | 2.5 | 1.2 | 1.7 | 1.1 | 1.4 | 1.4 | 1.8 | 1.9 | 2.4 |

Although the higher rate treatment generally provided a larger initial reduction in soil repellency, its effectiveness decreased rather rapidly as the season progressed.

The above results are illustrative of the enhanced longer-lasting water repellency reduction that can be achieved through the use of multiple low rate applications of the alkyl ethers of methyl oxirane-oxirane copolymers of the instant invention as opposed to split high rate applications of a hydroxy terminated commercial methyl oxirane-oxirane copolymer surfactant formulation.

EXAMPLE VIII

Figure 4:
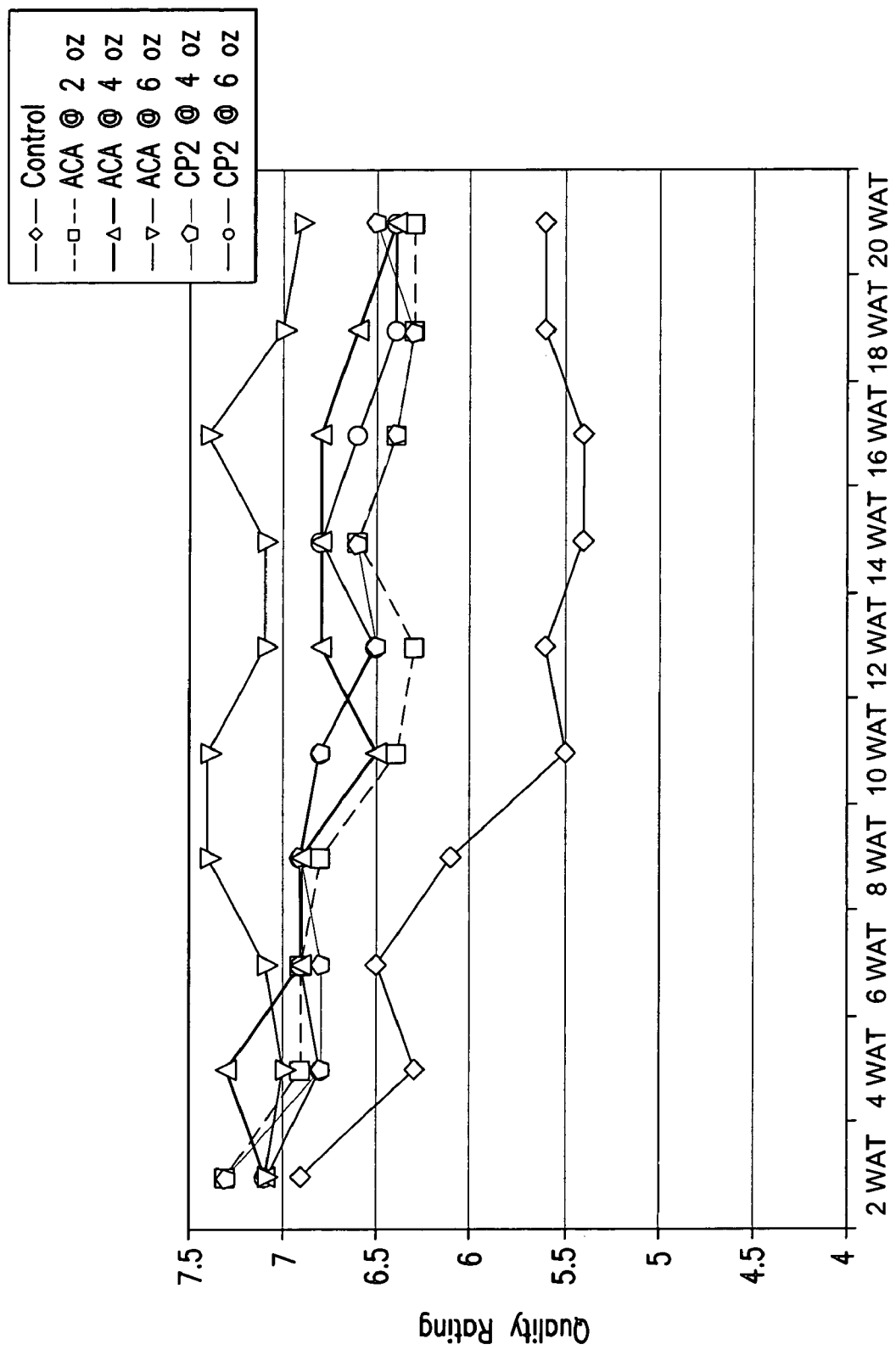
FIGS. 4-6 are graphical depictions of the turfgrass Quality results obtained by the tests in Example VIII and set forth in Tables VIIIA, B, and C.
Figure 5:
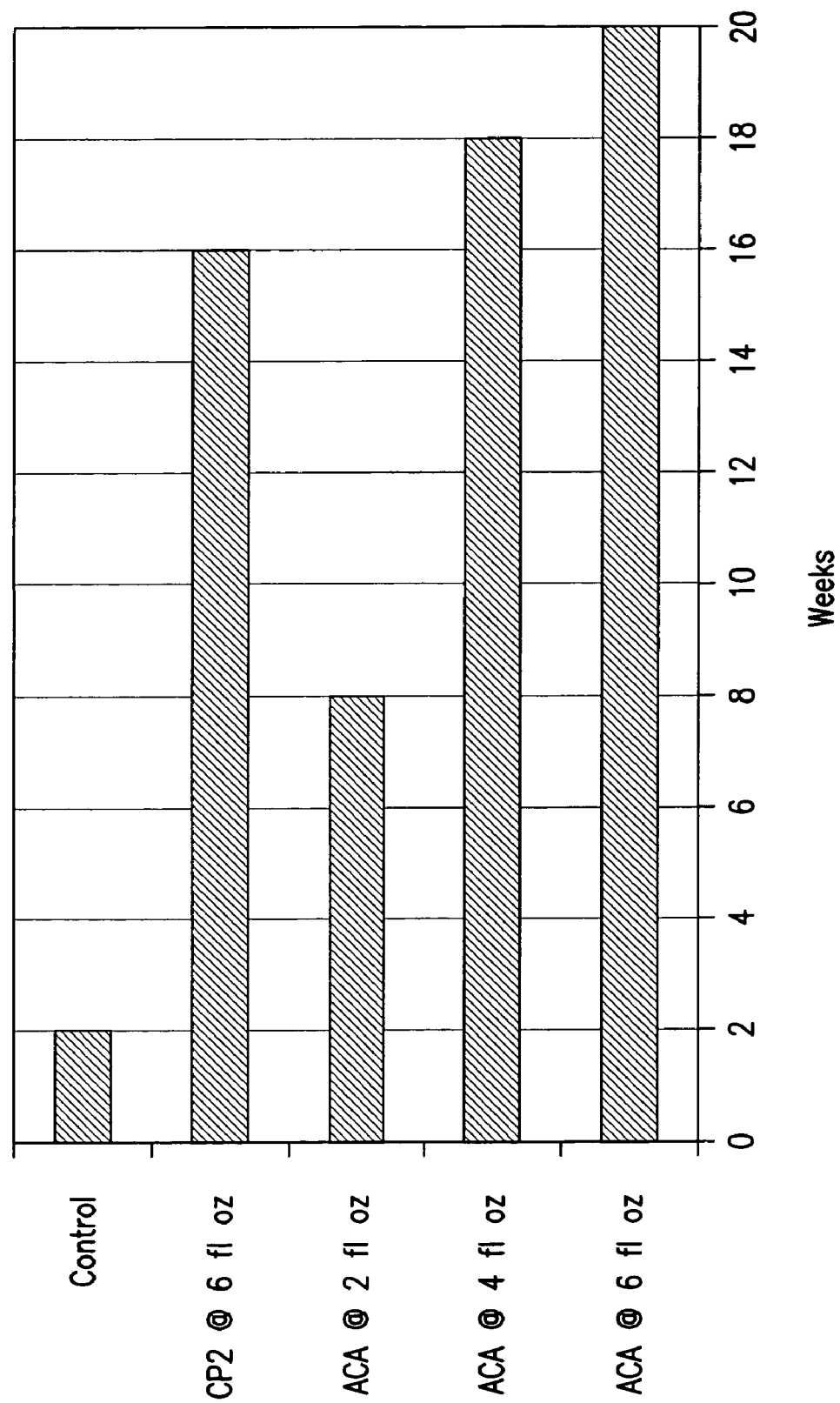
Figure 6:
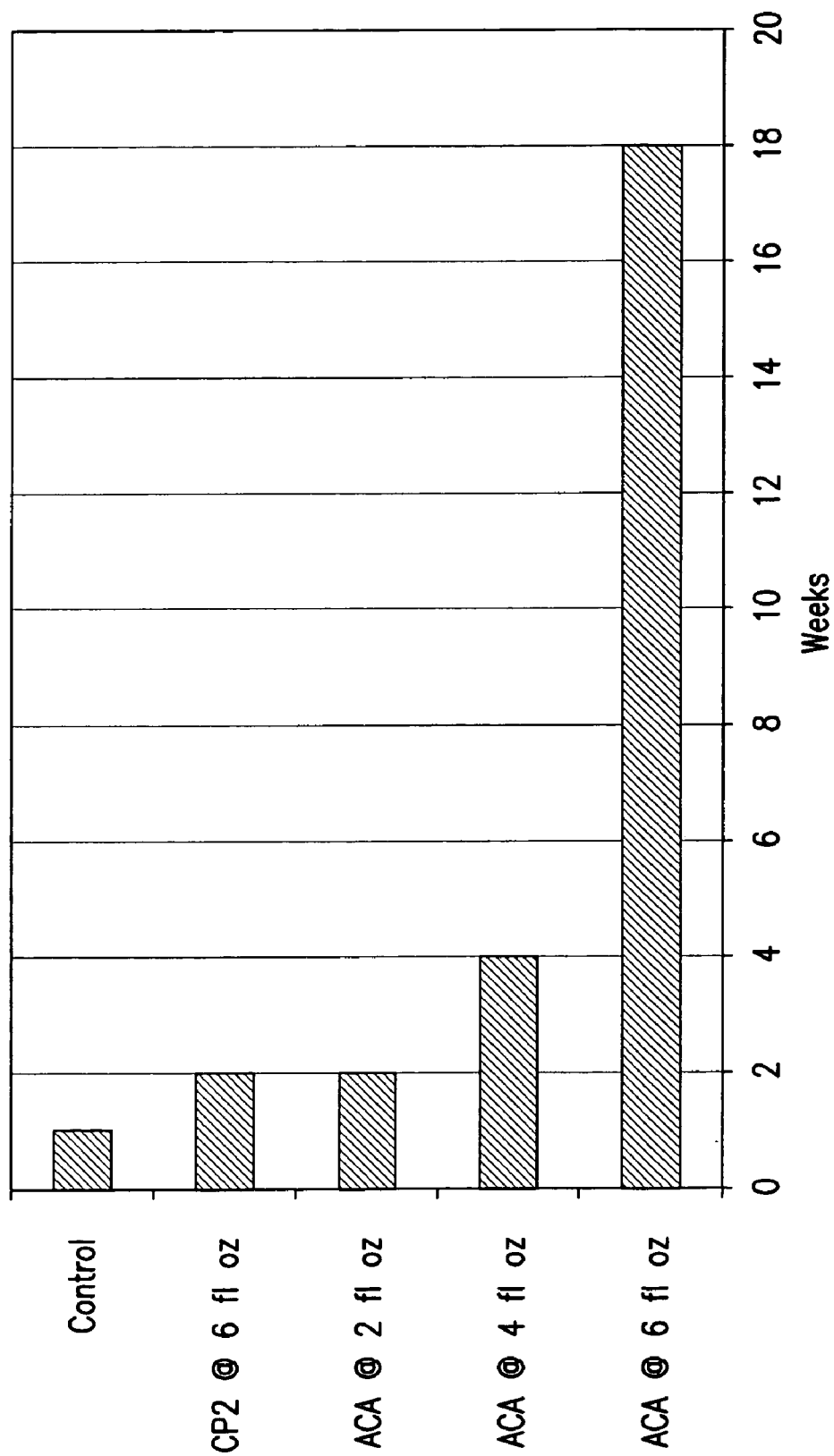

Field trials were conducted on a water repellent USGA specification green mix to ascertain whether the alkyl ethers of the methyl oxirane-oxirane copolymers of this invention had a measurable effect upon the quality of plant growth and if so, to what extent. For comparative purposes, results were also measured for plots with no surfactant treatment and for plots that had received applications of CP2. The turf that was the subject of the trials had been originally seeded with "Crenshaw" creeping bentgrass. The results set forth in Tables VIIIA, VIIIB, and VIIIC and depicted graphically in FIGS. 4 through 6 show the "Quality" rating of the turfgrass every two week(s) after treatment (WAT). The application rates were as indicated in the Tables and Figures. Each surfactant was applied four times during the season.

TABLE VIIIA

| Product/WAT | 2 | 4 | 6 | 8 | 10 | 12 | 14 | 16 | 18 | 20 |
|---|---|---|---|---|---|---|---|---|---|---|
| Control | 6.9 | 6.3 | 6.5 | 6.1 | 5.5 | 5.6 | 5.4 | 5.4 | 5.6 | 5.6 |
| CP2 @ 4 oz | 7.3 | 6.8 | 6.8 | 6.9 | 6.8 | 6.5 | 6.6 | 6.4 | 6.3 | 6.5 |
| CP2 @ 6 oz | 7.1 | 6.8 | 6.9 | 6.9 | 6.8 | 6.5 | 6.8 | 6.6 | 6.4 | 6.4 |
| ACA @ 2 oz | 7.3 | 6.9 | 6.9 | 6.8 | 6.4 | 6.3 | 6.6 | 6.4 | 6.3 | 6.3 |
| ACA @ 4 oz | 7.1 | 7.3 | 6.9 | 6.9 | 6.5 | 6.8 | 6.8 | 6.8 | 6.6 | 6.4 |
| ACA @ 6 oz | 7.1 | 7.0 | 7.1 | 7.4 | 7.4 | 7.1 | 7.1 | 7.4 | 7.0 | 6.9 |

Table VIIIB and Table VIIIC, together with their respective graphical representations set forth in FIGS. 5 and 6, show the number of weeks after treatment, in two week intervals, that the bentgrass turf maintained a Quality rating of 6.5 or higher and 7.0 or higher respectively.

TABLE VIIIB

| Product | Weeks After Treatment At Quality Rating Of 6.5 Or Higher |
|---|---|
| Control | 2 |
| CP2 @ 6 oz | 16 |
| ACA @ 2 oz | 8 |
| ACA @ 4 oz | 18 |
| ACA @ 6 oz | 20 |

TABLE VIIIC

| Product | Weeks After Treatment At Quality Rating Of 7.0 Or Higher |
|---|---|
| Control | 1 |
| CP2 @ 6 oz | 2 |
| ACA @ 2 oz | 2 |
| ACA @ 4 oz | 4 |
| ACA @ 6 oz | 18 |

The above results indicate the significant improvement in turf quality that can be obtained and sustained by the application of the alkyl ethers of the methyl oxirane-oxirane copolymers of the instant invention even when compared with the results obtained with the closest methyl oxirane-oxirane copolymer homologs, i.e., the hydroxy terminated methyl oxirane-oxirane copolymers. Not only did the Quality rating increase as the application rate increased, but the Quality rating increased dramatically at the four and six oz per 1000 square foot rates. Of major commercial importance and most surprisingly, at the six ounce rate, excellent turf quality was maintained for over four months.

EXAMPLE IX

Field studies were conducted on turf plots composed of a native sandy soil to determine the effects upon Local Dry Spots (LDS) by applications of the alkyl ethers of the methyl oxirane-oxirane copolymers of the instant invention. For comparison, additional plots were set aside for no treatment, i.e., control plots and for treatments with CP2 surfactant compositions at the 6 oz per 1000 square foot area. The ACA surfactant was applied at the rates indicated in Table IX. Treatments were applied monthly for four months. The initial percentage of the plots containing the Local Dry Spots was determined to be 6%. LDS percentage measurements were taken over a two and one-half month period from June through September. Table IX sets forth the average LDS levels observed at the end of the trials.

TABLE IX

| Product | Final Local Dry Spot (Percent) |
|---|---|
| Control | 11 |
| CP2 @ 6 oz | 6.7 |
| ACA @ 2 oz | 2.0 |
| ACA @ 4 oz | 1.0 |
| ACA @ 6 oz | 1.5 |

Obviously, the methyl ether of the methyl oxirane-oxirane copolymer of the instant invention managed to reduce significantly local dry spotting percentage in the plots tested, thus improving the uniformity and consistency of the turf. Of special note, the ACA applications at the 2 ounce per 1000 square foot area provided LDS control much superior to that provided by the commercial surfactant CP2 at the 6 ounce per 1000 square foot rate.

EXAMPLE X

Chemistries that reduce soil water repellency deeply into the soil enhance water movement off of the surface of the soil and thus deeper into the root zone of the plants. This moisture penetration is a highly desirable attribute in any plant growth medium and so a series of tests was established to determine how effective the alkyl ethers of the methyl oxirane-oxirane copolymers of this invention are relative to CP2 and CP4 surfactants in assisting surface water to penetrate the soil.

A number of field plots were established on a water repellent green built to USGA specifications and, after control plots were identified, certain plots were treated with CP2 (4 and 6 oz/1000 sq ft applied monthly for 4 months); other plots were treated with CP4 at an application rate of 8 oz/1000 sq ft at trial initiation and one week later; and the balance of the plots were treated with ACA at application rates of 2, 4, 6, and 8 oz/1000 sq ft monthly for four months. Every two weeks after the trial began, and during the full trial period of 20 weeks, WDPT measurements were made at 1 cm intervals on collected soil cores to determine the deepest depth in centimeters at which wetting was significantly faster that in the Control. The results of these tests setting forth the above-defined measurements on 14 day intervals for each treatment are recorded below in Table X.

The following denotation indicates the deepest site on the core that was significantly different from the untreated Control; "0" indicates the top of the core at the air/thatch interface and each negative number indicates the deepest consecutive depth (in centimeters) where water repellency is significantly lower than in the Control.

TABLE X

| Product/DAT | 14 | 28 | 42 | 56 | 70 | 84 | 98 | 112 | 126 | 140 |
|---|---|---|---|---|---|---|---|---|---|---|
| CP2 @ 4 oz | −2 | −3 | 0 | 0 | −2 | −1 | −2 | −4 | 0 | −3 |
| CP2 @ 6 oz | −2 | 0 | 0 | 0 | −2 | −2 | −2 | −4 | 0 | −2 |
| CP4 @ 8 + 8 oz | −4 | −2 | 0 | 0 | −2 | −1 | 0 | 0 | 0 | 0 |
| ACA @ 2 oz | 0 | 0 | 0 | 0 | −2 | −4 | −1 | −2 | −1 | −2 |
| ACA @ 4 oz | −2 | −1 | −1 | −1 | −2 | −2 | −4 | −4 | −4 | −3 |
| ACA @ 6 oz | −2 | −1 | −1 | −2 | −4 | −4 | −4 | −4 | −4 | −3 |
| ACA @ 8 oz | −3 | −3 | −1 | −3 | −4 | −4 | −4 | −4 | −4 | −3 |

The results of the depth measurement trials illustrate that alkyl ethers of methyl oxirane-oxirane copolymers improve receptivity to moisture deeper into soil matrices; and the soils wet more readily and for a more sustained period of time than when the CP2 and CP4 technologies are used.

EXAMPLE XI

To further characterize the ability of the alkyl ethers of the copolymers of this invention to penetrate soil matrices and sustain reduced water repellency at substantial depths below the surface, a series of tests were conducted on water repellent, USGA specification greens with applications of ACA and CP1, both applied at the rate of 8 oz per 1000 sq ft in two applications, each applied 1 week apart. Molarity of Ethanol Drop tests were used on samples taken from the treated (and untreated Control) every two weeks for a total test period of 20 weeks at two different depths, i.e., 0-1 cm and 1-2 cm. The MED results are set forth in Table XI for each depth and treatment compared to the untreated Control. Note that if any of the letter suffixes accompanying the MED values are not identical, one can state with a 95% confidence level that the numbers are significantly different.

TABLE XI

| Product/Weeks | 2 | 4 | 6 | 8 | 10 | 12 | 14 | 16 | 18 | 20 |
|---|---|---|---|---|---|---|---|---|---|---|
| Depth: 0-1 cm | | | | | | | | | | |
| CP1 | 0 c | 1.5 b | 1.4 b | 1.4 b | 2.0 b | 2.1 b | 2.2 a | 2.4 a | 2.7 a | 2.8 a |
| ACA | 0.1 b | 1.3 b | 1.2 b | 1.4 b | 1.7 b | 2.1 b | 2.0 a | 1.9 b | 2.5 a | 2.5 a |
| Control | 2.8 a | 2.9 a | 2.7 a | 2.8 a | 2.9 a | 2.6 a | 2.6 a | 2.7 a | 2.9 a | 3.0 a |
| Depth: 1-2 cm | | | | | | | | | | |
| CP1 | 0.2 b | 0.5 b | 0.5 b | 0.1 b | 0.5 b | 1.1 a | 1.3 a | 0.7 b | 1.1 a | 1.0 a |
| ACA | 0.1 b | 0.4 b | 0.5 b | 0.2 b | 0.8 b | 0.8 b | 1.0 a | 0.7 b | 1.2 a | 1.2 a |
| Control | 1.4 a | 1.4 a | 1.3 a | 1.5 a | 1.4 a | 1.5 a | 1.4 a | 1.5 a | 1.4 a | 1.4 a |

Both CP1 and ACA reduced soil water repellency in the 0-1 and 1-2 cm depths in the rootzone. At the 0-1 cm depth, CP1 was effective (as compared to the Control) on 6 of 10 measurement dates (up to 12 weeks), while ACA was effective on a total of 7 of 10 dates (up to 12-16 weeks). Deeper in the rootzone (1-2 cm) soil water repellency was significantly reduced by CP1 on 6 of 10 dates, while ACA reduced water repellency on 7 of 10 dates. In both cases, ACA provided longer term performance than the unmodified version. This longer performance is likely due to the slower rate of biodegradation for ACA.

EXAMPLE XII

ACA has been demonstrated to biodegrade slowly (30-40% over 28 days). The following trial is to determine the consequence of this on surfactant performance in treated soils.

A replicated trial was conducted on fairway height bentgrass growing on a sandy soil in the transition zone. Surfactant applications were applied monthly beginning in early May, then at approximately 28-day intervals for the next four months, with the last application being in early September. Six months later (March), soil cores were sampled from treated and untreated plots and soil water repellency determined by WDPT.

The below Table XII outlines the results of the WPDT test in the 0.1 cm region of the soil profile. Note that if any of the letter suffixes accompanying the WDPT second values are not identical, one can state with a 95% confidence level that the numbers are significantly different.

TABLE XII

| Product | WPDT Values (sec.) | 95% Confidence Level |
|---|---|---|
| Control | 111.4 | b |
| CP2 @ 4 oz | 78.5 | ab |
| CP2 @ 6 oz | 52.8 | ab |
| ACA @ 2 oz | 49.2 | ab |
| ACA @ 4 oz | 28.3 | a |
| ACA @ 6 oz | 20.7 | a |
| ACA @ 8 oz | 27.1 | a |

Six months after the final treatment application, statistically significant differences (LSD, p=0.1) in soil water repellency were observed between treatments. Soil water repellency in CP2 (4 oz and 6 oz/1000 sq ft) and ACA (2 oz/1000 sq ft) treated soils was statistically equivalent to the untreated control. However, in soils treated with higher rates of ACA (4 oz/1000 sq ft or greater) significantly lower soil water repellency were found. The significance of this finding is that soils receiving five "in season" treatments of ACA at 4 oz or higher, will remain wettable during the winter months when irrigation systems are shut down. Agronomically and hydrologically, the observed "long-term" reduction in soil water repellency, clearly indicates that Critical Water Content can be modified for extended periods by this chemistry. This means that any rainfall that may occur has a higher potential to effectively and rapidly infiltrate treated soils. In regions where water restrictions are in place or under drought, this increase in wettability can have considerable impact on water conservation and rootzone recharge.

If one is trying to maximize water inputs and limit outputs, the ramifications of these observations on the invention may be staggering.

EXAMPLE XIII

Figure 7:
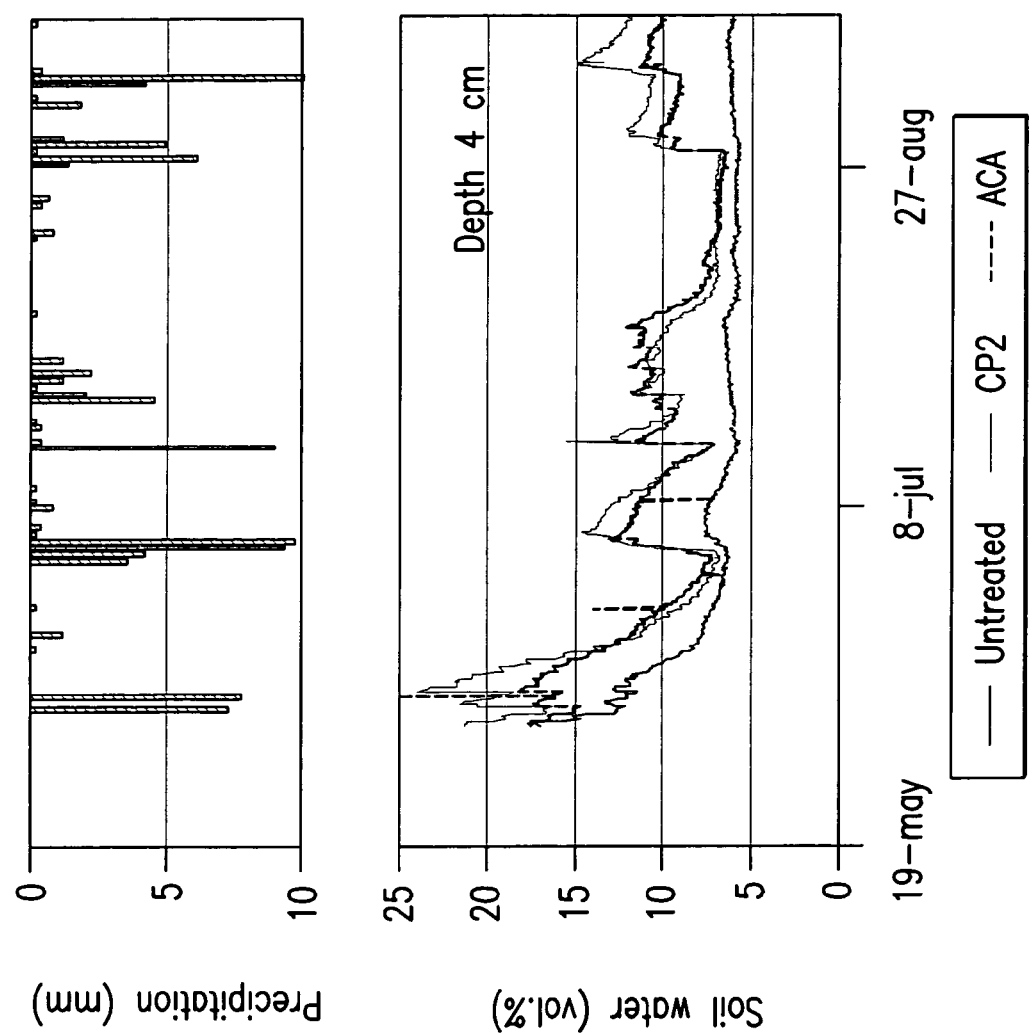
FIGS. 7 and 8 are graphical depictions of the volume percent water and precipitation results obtained by the tests on fairway turfgrass explained in Example XIII.

Three 8'×10' plots of soil containing a fairway turf grass growing on a sandy native soil were selected and studied for a period of two and one-half months. At the beginning of the test period, one plot was treated with CP2 surfactant at a rate of 6 ounces per 1000 square feet; the second plot received an application of ACA surfactant also at 6 ounces per 1000 square feet; and the third plot left untreated as a Control. Throughout the entire test period, continuous measurements were made of the natural rainfall precipitation that the areas received as well as the soil water in volume percent at a level 4 centimeters below the surface. The results of the continuous data plots are shown in FIG. 7. Furthermore, the total amount of water increase realized during the entire trial period expressed in millimeters of water, was measured and calculated for four different layers of the soil, to wit, in the 0-7 cm layer, the 7-15 cm layer; the 15-25 cm layer; and the 25-35 cm layer. This data is set forth in the bar chart in FIG. 8.

It was observed that even with numerous days of precipitation, the soil at the 4 cm level in the untreated plot had dried to the point at which it was unable to be re-wetted with water alone, i.e., the Critical Water Content had been reached. However, with the plots that had been treated with the surfactants, after every precipitation event, the volume percent of the water in the soil increased, i.e., the soil re-wetted. Both surfactants were able to modify the CWC levels of the soil.

Interestingly, with each new precipitation event, the volume of water held by the soil that had been treated with the hydroxy terminated CP2 surfactant composition, initially was more than that in the soil that had been treated with the alkyl ether ACA copolymer; although in a short period of time the former levels dropped and the water volume levels became comparable in the two treated plots.

Figure 8:
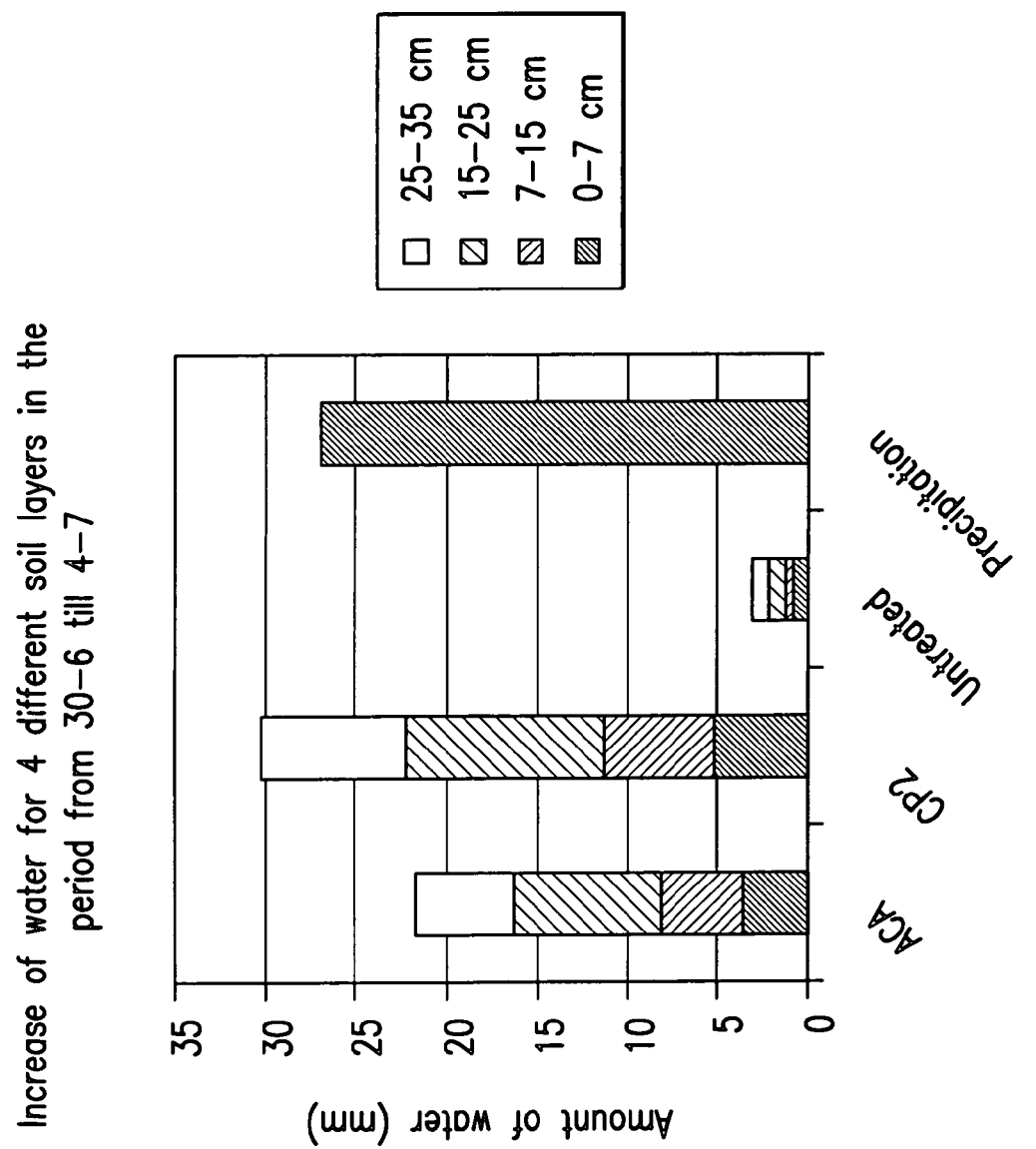

The FIG. 8 data, which reflects the total increase of water during the test period at four layers, confirmed the above observation at the 4 cm level. The CP2 surfactant enabled the soil to retain more water when measured over the whole test period than the soil that had been treated with the ACA surfactant. One would expect that the additional water would enhance the turf quality and density, however it was observed that, surprisingly, this was definitely not the situation. The Quality rating of the turf growing in the soil that had been treated with the alkyl ether of the methyl oxirane-oxirane copolymer ACA was far superior to that of the turf growing in the soil that had been treated with CP2, the hydroxl terminated methyl oxirane-oxirane copolymer.

To objectively confirm the visual observations, 50 cm×50 cm areas were delineated on each of the test plots and a physical count was made of the number of shoots of grass per square inch for each area. The results were striking as shown in the following Table XII.

TABLE XII

| Turf Plot | Shoots per square inch |
| --- | --- |
| Control | 7 |
| CP2 Treated @ 6 oz/1000 sq ft | 14 |
| ACA Treated @ 6 oz/1000 sq ft | 21 |

Thus, i) although both CP2 and ACA surfactant compositions were able to reduce the water repellency of the soil, and to modify the Critical Water Content of the soil; and ii) the ACA treated soils hold less water by volume than the CP2 treated soils; the turf quality and density in the ACA treated soil is significantly superior to that achieved with the CP2 treated soil. In other words, the $C_1$ to $C_4$ alkyl ethers of the methyl oxirane-oxirane copolymers, when added to soil, significantly and unexpectedly improve the plant growth characteristics of the soil.

Soil water content analysis also indicated that to the 5 cm depth in horizontal planes, a very homogeneous moisture content level existed with the ACA treated soils, i.e., 90% of the moisture content measurements were in the 16 to 24 volume percent range. Serendipitously, this corresponds closely to the USGA Greens Section Physical Properties recommendation of 15 to 25% moisture content in the rootzone.

Although the inventors do not intend to be bound or limited by the following, it is suggested that the experimental data provided in the Examples set forth above indicate that a number of growth promoting characteristics and/or properties of soils treated with the alkyl ethers of the methyl oxirane-oxirane copolymers have been unexpectedly enhanced.

At the outset, the micro-extraction results in Example I strongly suggest that the alkyl ether copolymers of this invention solubilized certain components in the soil, quite possibly nutritional compounds for the plants. Examples II, III, IV, X, XI, XII and XIII show rapid and penetrating re-wetting properties associated with the alkyl ether copolymers yet they do not hold excessive amounts of water in the soil, i.e., the soil is possibly better aerated than saturated, soggy soil—a common complaint associated with the use of many agrochemical surfactants.

In summary, and as a result of these phenomena, it is suggested that when the alkyl ethers of the methyl oxirane-oxirane copolymers of this invention are added to the plant growth medium, the medium surrounding and within the plant root zone becomes significantly enhanced by quickly and uniformly providing additional solubilized nutrients with sufficient moisture i) to continually provide water per se to the plant and ii) to act as a transport mechanism for the additionally solubilized nutrients. Alternatively, or additionally, the alkyl ethers of the copolymers may be affecting the root transport mechanisms directly.

It is also suggested that the slow release characteristics of these alkyl ether copolymers, as has been discussed above, also contribute to the increased quality and density of the plants, for the continuity of the concentration in the soil with its attendant enhancement properties, avoids the stress that plants experience in rapidly and/or constantly changing environments.

It is anticipated that the alkyl ethers of the methyl oxirane-oxirane copolymers of this invention can also be blended with soil active or soil directed pesticides.

It is also anticipated that the liquid compositions of the instant invention be also utilized in solid form, e.g., powder or granular form, by either being added to and/or blended with inert filler material, biological actives, such as pesticides, and/or other additives, such as adjuvants in methods well known by those skilled in the agrochemical water dispersible or dry spreadable art. In this way, the compositions are able to be delivered in solid form to the plant growth medium and additional control of the release of the compositions can be achieved if one so desires.

Although this invention has been described in detail with particular reference to preferred embodiments thereof, it will be understood that variations and modifications can be effected within the spirit and scope of this invention as described hereinabove and as defined in the appended claims.

Having thus described the invention, what we claim is:

1. A method for enhancing plant growth in plant growth medium which comprises the steps of:
   i) preparing a surfactant composition comprising $C_1$-$C_4$ alkyl ether of methyl oxirane-oxirane copolymer; and
   ii) intimately contacting the plant growth medium with a bioefficaciously effective amount of said surfactant composition.

2. The method of claim 1 wherein the effective amount of surfactant composition is from about 0.001 to about 128 fluid ounces per 1000 square feet.

3. The method of claim 1 wherein the effective amount of surfactant composition is from about 0.2 to about 16 fluid ounces per 1000 square feet.

4. The method of claim 1 wherein the plant growth medium is water repellent soil.

5. The method of claim 1 wherein the surfactant composition additionally contains water.

6. The method of claim 1 wherein the $C_1$-$C_4$ alkyl ether of methyl oxirane-oxirane copolymer is prepared by the etherification of a copolymer comprising a straight polymeric glycol obtained by the addition of oxirane on polymethyloxirane.

7. The method of claim 1 wherein the surfactant composition additionally contains soil active or soil directed pesticide.

8. An improved plant growth medium comprising
   i) plant growth medium; and
   ii) a bioefficaciously effective amount of a surfactant composition comprising $C_1$-$C_4$ alkyl ether of methyl oxirane-oxirane copolymer.

9. The improved plant growth medium of claim 8 wherein the effective amount of the surfactant composition is from about 0.001 to about 128 fluid ounces per 1000 square feet of plant growth medium.

10. The improved plant growth medium of claim 8 wherein the plant growth medium is water repellent soil.

11. The improved plant growth medium of claim 8 wherein the $C_1$-$C_4$ alkyl ether of methyl oxirane-oxirane copolymer is prepared by the etherification of a copolymer comprising a straight polymeric glycol obtained by the addition of oxirane on polymethyloxirane.

12. The improved plant growth medium of claim 8 wherein the surfactant composition additionally contains soil active or directed pesticide.

13. A method for improving the re-wetting properties of plant growth medium which comprises the steps of:
   i) preparing a surfactant composition comprising $C_1$-$C_4$ alkyl ether of methyl oxirane-oxirane copolymer; and
   ii) intimately contacting the plant growth medium with a re-wettingly effective amount of said surfactant composition.

14. The method of claim 13 wherein the effective amount of surfactant composition is from about 0.001 to about 128 fluid ounces per 1000 square feet.

15. The method of claim 13 wherein the effective amount of surfactant composition is from about 0.2 to about 16 fluid ounces per 1000 square feet.

16. The method of claim 13 wherein the plant growth medium is water repellent soil.

17. The method of claim 13 wherein the surfactant composition additionally contains water.

18. The method of claim 13 wherein the $C_1$-$C_4$ alkyl ether of methyl oxirane-oxirane copolymer is prepared by the etherification of a copolymer comprising a straight polymeric glycol obtained by the addition of oxirane on polymethyloxirane.

19. The method of claim 13 wherein the surfactant composition additionally contains soil active or directed pesticide.

* * * * *